United States Patent [19]

Alving et al.

[11] Patent Number: 5,229,376
[45] Date of Patent: Jul. 20, 1993

[54] ENCAPSULATED PLANT-DERIVED PHOSPHATIDYLINOSITOL (PI) COMPOSITIONS FOR THE PREVENTION OF MITOGENICALLY INDUCED CELL PROLIFERATION

[75] Inventors: Carl R. Alving, Bethesda, Md.; Earl C. Richardson, Darby, Mont.

[73] Assignee: The United States of America as represented by the Secretary of the Army, Washington, D.C.

[21] Appl. No.: 667,894

[22] Filed: Mar. 12, 1991

Related U.S. Application Data

[60] Continuation-in-part of Ser. No. 168,079, Mar. 14, 1988, Pat. No. 4,999,344, which is a continuation-in-part of Ser. No. 117,601, Nov. 6, 1987, abandoned, which is a division of Ser. No. 911,689, Sep. 25, 1986, abandoned.

[51] Int. Cl.$^5$ .............. A01N 57/26; A61K 31/685
[52] U.S. Cl. ........................ 514/76; 514/77; 514/78; 552/506; 552/544
[58] Field of Search .............. 514/77, 76, 78; 552/506, 544

[56] References Cited

U.S. PATENT DOCUMENTS 4,999,344 3/1991 Jett-Tilton et al. ............... 514/77

Primary Examiner—Nathan M. Nutter
Attorney, Agent, or Firm—John F. Moran; Werten F. W. Bellamy; Anthony T. Lane

[57] ABSTRACT

Encapsulated PI compositions such as liposomes containing plant PI and their use to prevent mitogenic transformation of normal splenic lymphoid cells (including lymphocytes transformed induced by treatment of cells with lipid A) by exposing the cells thereto.

11 Claims, 3 Drawing Sheets

ENCAPSULATED PLANT-DERIVED PHOSPHATIDYLINOSITOL (PI) COMPOSITIONS FOR THE PREVENTION OF MITOGENICALLY INDUCED CELL PROLIFERATION

GOVERNMENT INTEREST

The invention described herein may be manufactured, licensed and used by or for governmental purposes without the payment of any royalties to us thereon.

RELATED APPLICATION(S)

This application is a continuation-in-part of U.S. patent application Ser. No. 07/168,079 filed Mar. 14, 1988 and now U.S. Pat. No. 4,999,344 which in turn is a continuation-in-part of U.S. patent application Ser. No. 07/117,601, filed Nov. 6, 1987, and now abandoned, which is a division of Ser. No. 06/911,689, filed Sep. 25, 1986 now abandoned.

TECHNICAL FIELD OF INVENTION

This invention relates to encapsulated plant-derived Phosphatidylinositol (PI) compositions for the prevention of mitogenically-induced cell proliferation.

BACKGROUND OF THE INVENTION

Throughout the world, diseases caused by mitogenically-induced cells including any cell that (1) proliferates in responses to exposure or infection with a virus, (2) is induced to proliferate to a malignant state by exposure to a mitogenic substance or (3) is induced to proliferate because of exposure to any nonspecific mitogenic stimulus are the major causes of illness and death.

DEFINITION

The following definitions set forth herein below apply to the defined terms as used throughout this application:

Mitogens: Mitogens are "substances which cause cells, particularly lymphocytes, to undergo cell division" (Roitt, I. M., Brostoff, J., and Male, D. K. "Immunology", 2nd Ed., C. V. Mosby, 1989, Glossary). Substances that have the "ability to convert quiescent cells into growing and dividing "blasts" are commonly referred to as mitogens (Di Sabato, G., Hall, J. M., and Thompson, L., Methods in Enzymology, 187:3, 1987). The mitogenic process results in a activation of lymphocytes and other cells, and such activated cells have remarkable similarities to and are often considered to be models of: cells that have been stimulated to proliferate by exposure to antigen; cells that have been stimulated to proliferate by exposure to viruses; cells that have been stimulated to proliferate by exposure to other cells that have been previously activated; tumor cells and other rapidly proliferating cells that have been stimulated to proliferate because of the malignant state; and cells that have been caused to proliferate because of numerous so-called "Nonspecific" mitogenic stimuli, such as plant lectins, bacterial lipopolysaccharides (of which the lipid A moiety is the active fraction), heavy metal ions, ionophores, proteolytic enzymes, antibodies to membrane components, and many others.

Lymphocyte activation (also referred to as lymphocyte stimulation or transformation): So-called nonspecific mitogenic stimulation of lymphocytes has been widely studied in the literature both as a model of the mitogenic process, and as a model of the process of immunological functioning of lymphocytes in health and disease. The process, and its similarities and differences compared to viral transformation of cells and to malignant transformed cells have been the subject of thousands of scientific studies (e.g., reviewed in Ling, N. R., Kay, J. E., Lymphocyte Stimulation, 2nd Ed., American Elsevier, N.Y., 1975; Wedner, H. J., and Parker, C. W., Lymphocyte Activation, Prog. Allergy 20:195-300, 1976; Hume, D. A. and Weidemann, M. J., Mitogenic Lymphocyte Transformation, Research Monographs in Immunology, Vol. 2, Elsevier/North-Holland, Amsterdam, 1980; and in Di Sabato, editor, Immunochemical Techniques, Part K. In Vitro Models of B and T Cell Functions and Lymphoid Cell Receptors, Methods in Enzymology, Vol. 150, Academic Press, NY 1987.) Among the many interesting properties of activated normal lymphocytes are the excretion of DNA from the cells in response to mitogenic stimulus, and it is has been hypothesized that such excreted DNA might function in the passage of genetic information between cells (Wedner and Parker, 1976, p. 255).

Lectins: "Plant lectins are divalent or polyvalent carbohydrate-binding proteins of plant or animal origin that are extensively used in biological research. Although a wide variety of biological effects has been ascribed to these substances, lectins are primarily used for . . . their mitogenic activity on lymphocytes." (Di Sabato et al, 1987). As pointed out by Parker (1987) "Because of their commercial availability and marked stimulatory activity and marked stimulatory activity lectins such as phytohemagglutinin (PHA), concanavalin A (Con A) and pokeweed (PW) have gained wide popularity for metabolic studies." These lectins are particularly noted for their differential ability to cause activation of T lymphocytes.

B cell mitogens: The most commonly used mitogen used for stimulation of B lymphocytes is lipopolysaccharide (LPS) derived from Gram-negative bacterial cells. The active site of LPS is the lipid A moiety and LPS (lipid A) commonly used for inducing mitogenic stimulation of cells. Lipid A was employed in all of the studies described in this disclosure.

SUMMARY OF THE INVENTION

Applicants have discovered that they have been able to prevent mitogenic transformation of normal splenic lymphoid cells (including lymphocytes transformed induced by treatment of cells with lipid A) by exposing the cells to encapsulated PI compositions such as liposomes containing plant PI. The active portion of the formulation constituted of the plant PI. When PI derived from animal sources was substituted for plant-derived PI, suppression of mitogenesis was markedly diminished or absent. Furthermore, the degree of suppression of mitogenesis was dependent on the concentration of PI in the liposomes. Based on the known differential composition of plant compared to animal PI (Jett, M., Chudzik, J., Alving, C. R., and Stanacev, N. Z., Cancer Res. 45:4810-4815, 1985; Jett-Tilton, M. and Alving, C. R., U.S. Pat. No. 4,999,344) we propose that the liposomes and liposomal PI compositions that would be effective in the present stipulation are the same as those described in Jett-Tilton, M. and Alving, C. R., U.S. Pat. No. 4,999,344.

Therefore, one embodiment of the present invention comprises a method for inhibiting the mitogenic transformation of normal mammalian cells, said method comprising contacting said cells with a cell proliferating inhibiting amount of a diacyl phosphatide, wherein the sn2-acyl group is a polyunsaturated fatty acid, said contacting being in the substantial absence of non-phosphatidic fatty acid esters having fewer than 2 olefinic sites of unsaturation in the fatty acid of said ester, for a sufficient time to inhibit said transformation.

DETAILED DESCRIPTION OF THE INVENTION-EXAMPLES

Figure 1:
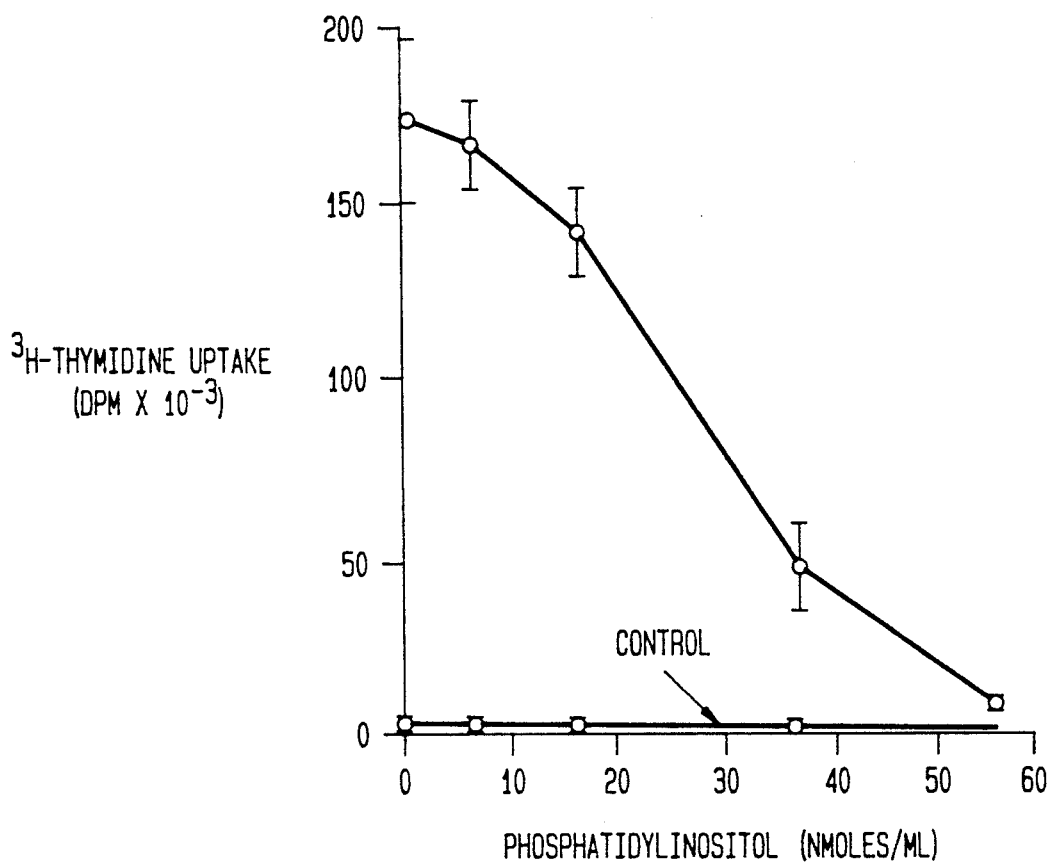
FIG. 1 shows suppression of lymphocyte mitogenesis. The results are expressed as the geometric mean of disintegrations per minute plus or minus standard error of the mean. The control values were obtained in the absence of lipid A. The PI was in the form of liposomes that consisted entirely of phosphatidylinositol from plant origin The open circles represent cell cultures in which 0.5 nmoles of lipid A phosphate/ml was present. The lipid A had been solubilized in 0.5% triethylamine. The control cells (closed circles) were incubated with PI in the absence of lipid A. Details of mitogenic assays that we use have been published by Richardson, E. C. and Alving, C. R., Mitogenic response of lymphocytes from C3H/HeJ mice in the presence of lipid A and lipid A fractions. Rev. Infect. Dis. 6:532–534 (1984).
Figure 2:
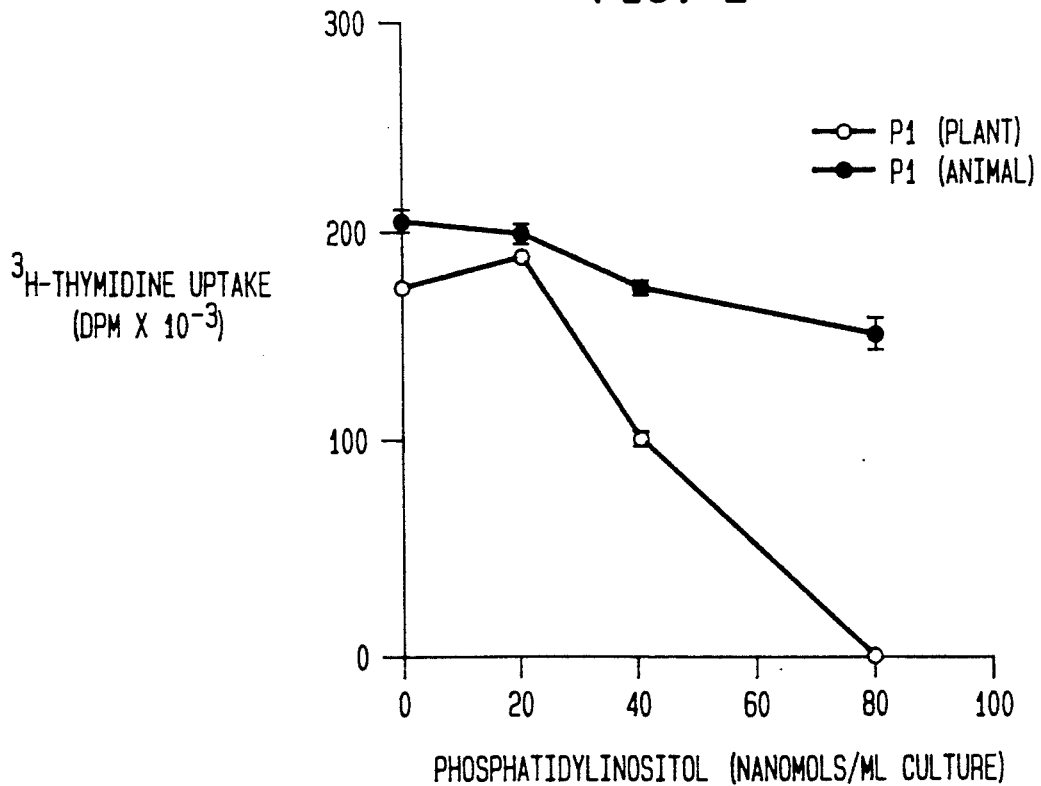
FIG. 2 shows the inhibition of the mitogenic effects of lipid A on mouse spleen lymphocytes by phosphatidylinositol.
Figure 3:
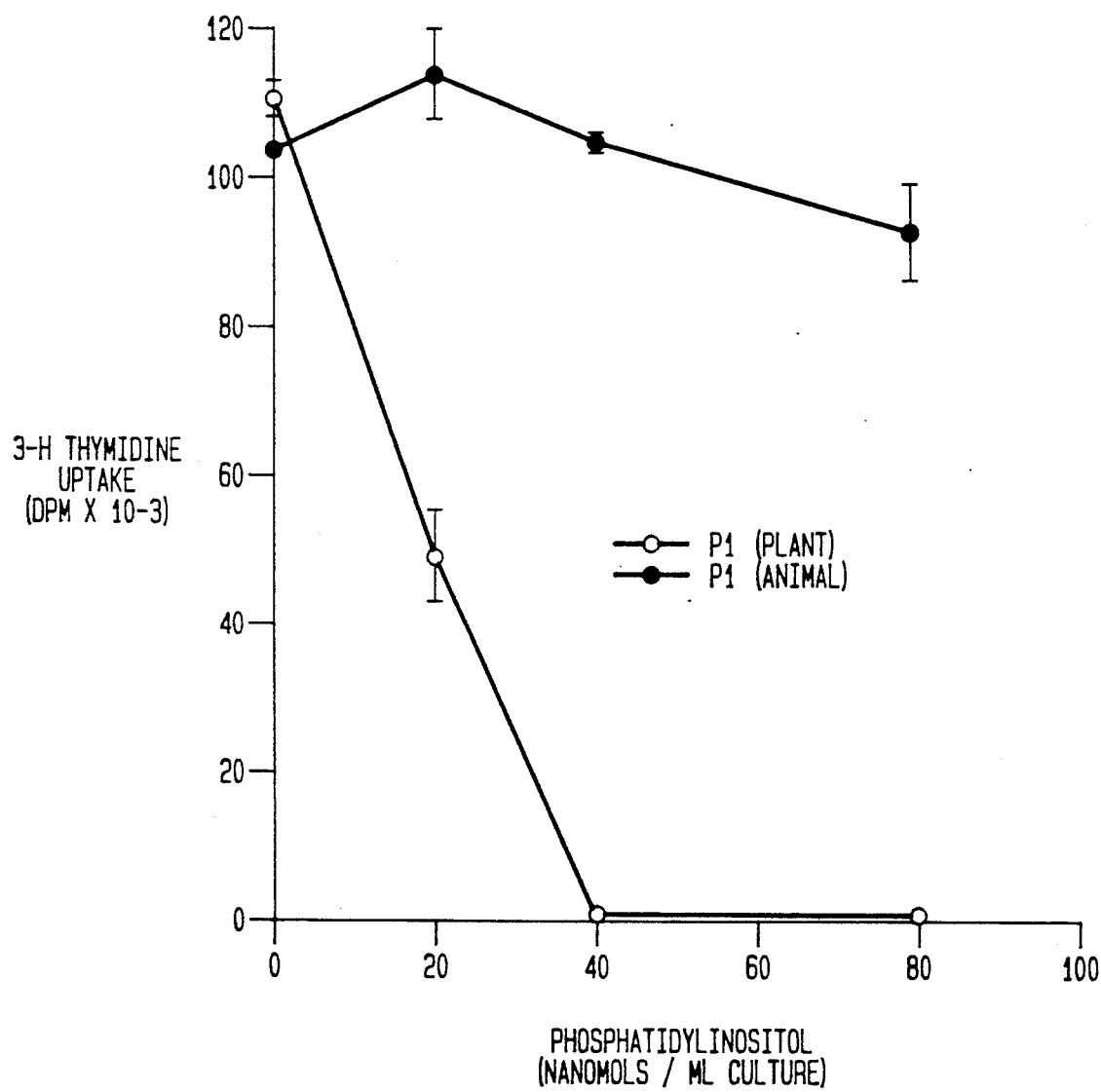
FIG. 3 shows the inhibition of the mitogenic effects of PH on mouse spleen lymphocytes by phosphatidylinositol.

The herein offered examples provide methods for illustrating, without any implied limitation, the practice of this invention in the prevention of mitogenic transformation of normal splenic lymphoid cells (including lymphocytes transformed induced by treatment of cells with lipid A) by exposing the cells to encapsulated PI compositions such as liposomes containing plant PI.

Phosphatidyl compounds having sensitivity to phospholipase A2 would be expected to have activity in this invention. This is based on the known difference between plant PI and animal PI has having been identified as being differential sensitivity to phospholipase A2 because of the highly unsaturated sn-2 fatty acid (mainly linoleic acid) of plant PI. This would result in the production of breakdown products of PI (or other phosphatidyl compounds) (specifically, lysoPI and free fatty acid) that have biological activities that affect cells. Other parent phosphatidyl compounds that could have phospholipase A2 sensitivity include: phosphatidylcholine, phosphatidic acid, phosphatidylserine, phosphatidylglycerol, cariolipin, and any synthetic phosphatidyl compounds that express sensitivity to phospholipase $A_2$.

The differential sensitivity of cells to phosphatidyl compounds having unsaturated sn-2 fatty acids to phospholipase A2, resulting in differential cytotoxicity to tumor cells, has been reduced to practice and taught in detail in the literature [Jett, M., Chudzik, J., Alving, C. R., and Stanacev, N. Z., Cancer Res. 45:4810-4815, 1985; and by Jett-Tilton, M. and Alving, C. R., U.S. patent application No. 07/168,079; and by Jett, M. and Alving, C. R. Tumoricidal effects of liposomes containing phosphatidylinositon or phosphatidylcholine, Meth. Enzymol. 141;459-466, 1987; and by Jett, M. and Alving, C. R., Phospholipase A2 substrates; a novel approach to cancer chemotherapy. In, "Liposomes as Drug Carriers", G. Gregoriadis, editor, John Wiley & Sons, London, 1988, pp. 419-429].

The phospholipase $A_2$-sensitive phosphatidyl compounds must have the ability to be presented in a form in which the enzyme can gain access to the phosphatidyl compound substrate. This can be readily achieved either in vitro or in vivo by inclusion of the phosphatidyl compound substrate in a liposome, with the phosphatidyl compound either constituting the entire liposome by itself, or by constituting only one of a group of lipids in the liposome. The other lipids in the liposome could include other phosphatidyl compounds, glycolipids, sterols such as cholesterol, fatty acids, diglycerides, triglycerides, and synthetic lipid molecules that provide a particulate dispersion in water. In addition, presentation of the phosphatidyl compound in the presence of a detergent could serve to enhance the activity by dispersing the compound in a finer suspension or micellar form that would provide a greater surface area for the enzyme-substrate reaction to occur. The phospholipase $A_2$-sensitive phosphatidyl compounds could also be presented in the form of lipospheres. In the latter formulations, the lipospheres consist of a hydrophobic core lipid (e.g., trilycerides) in which the surface of the lipid particle is covered with phospholipids. The phospholipids on the liposphere surface could include phospholipase $A_2$-sensitive phosphatidyl compounds.

APPLICATIONS AND METHODS FOR USING THIS INVENTION.

It is contemplated that this invention could be used under any circumstances in which cells are specifically or nonspecifically induced to undergo proliferation as a result of mitogenic stimuli The purpose of the invention is to prevent the initiation of proliferation either before or after the exposure of the cell to the mitogenic agent. Circumstances where this occurs include: virtually all forms of virus infection, including infection with HIV, dengue virus, influenza virus, EB virus, etc., proliferation that is caused by the malignant state. Although the exact mitogenic stimulus responsible for malignant proliferation cannot always be identified, it is recognized that immune responses to cell surface antigens, which almost invariably occurs as a result of malignant transformation, is inn itself a potent mitogenic stimulus. The malignant state sometimes is thought to be caused by virus infection (e.g., Epstein-Barr virus is thought to be the causative agent of both an lymphomatous tumor that is particularly widespread in China, and also is responsible for infectious mononucleosis). The malignant condition is generally considered to have been induced by mitogenic stimuli that cause malignant transformation, and the continuous proliferative condition may result from continuous mitogenic stimuli. Exposure of lymphoid cells to antigens represents a classical mitogenic stimuli for the cells to undergo proliferation. There are numerous autoimmune diseases (e.g., lupus erythrmatosus, rheumatoid arthritis, etc.) that are caused by abnormal proliferation of lymphooyte clones that secrete autoantibodeis. Phosphatidyl treatment of such conditions would be expected to interrupt the mitogenic stimuli responsible for proliferation.

The utilization of this invention is quite simple. It is only necessary to allow the appropriate phosphatidyl compound to be exposed to the cell that is desired to be suppressed in its proliferation by mitogenic stimuli. This is done in tissue culture by adding the phosphatidyl compound to the cells prior to or shortly after initiation of exposure to the mitogenic stimulus. In vivo, the situation would depend on the particular goal. For prevention of growth of malignant cells due to exposure to other malignant cells or due to other mitogenic stimuli (such as tumors arising from exposure to HIV), the phosphatidyl compound would be administered as a prophylaxis or treatment just as any other drug is administered. For example, systemic administration by intravenous infusion would provide global systemic protection against the mitogenic induction of cell proliferation. In a case where viral prophylaxis would be desired, the phosphatidyl compound could be administered in the same fashion. The treatment could also be administered locally. For example, direct infusion or implantation (subcutaneous, intramuscular, intradermal, or other local delivery method) could be employed to deliver the phosphatidyl compound to identified sites of lesions derived from HIV infection, herpes simplex infection, etc.

The phosphatidyl compound could also be used to prevent cell proliferation resulting in abnormal production of antibodies by lymphocytes. For example, local secretion of immunoglobulins or inflammatory mediators in joint cavities that are at risk for developing arthritis (e.g., rheumatoid or osteoarthritic joints This could be employed as a means to prevent pathological immune reactions due to secretion of autoantibodies by lymphocytes in autoimmune diseases, such as lupus erythrymatosus or rheumatoid arthritis.

It should be pointed out that the purpose of this invention is to prevent proliferation of cells that are induced to proliferate by mitogenic stimuli. This invention therefore differs from U.S. Pat. No. 4,999,344 filed Jul. 14, 1988, entitled "Phosphatidyl Treatment of Rapidly Proliferating Cells", Marti Jett-Tilton and Carl R. Alving, inventors. In the latter invention, plant PI is used to treat cells that already in the proliferative state and the treatment results in the killing of the proliferating cell. The present invention would act at a stage prior to the onset of proliferation and prevents proliferation of the cell. However, it is likely that most of the presumed commercial situations in which the two inventions would be utilized would be similar. The prevention of proliferation in the present invention would be presumed to be the more important step. For example, it would be preferable to prevent malignant proliferation rather than to treat already proliferating cells. Likewise it would be preferable to prevent proliferation of virus-exposed cells. Likewise it would be preferable to prevent proliferation of virus-exposed cells than to wait to kill cells that have heavy virus infections.

The present disclosure of suppressive effects of plant PI on mitogenic stimulation of cells predicts the prophylactic suppressive effect of plant PI on proliferation of cells induced by viral mitogenic effects, or educed by malignant mitogenic effects, and mitogenic effects induced by a wide range of other stimuli.

EXAMPLES DEMONSTRATING REDUCTION TO PRACTICE

EXAMPLE 1

Please note that in addition to the examples that are attached, the original reduction to practice, along with teaching relating to the methodology, are embodied within the manuscript submitted to *Science* on Mar. 18, 1981.

Liposomes (phospholipid bilayer vesicles) have been proposed by numerous laboratories as carriers of drugs and other substances for various clinical applications. Among the earliest suggestions, and one that still enjoys a measure of popularity, was that enzymes encapsulated within liposomes might be delivered efficiently for treatment of disorders in which the enzymes are lacking.

Among potential problems in the use of liposomes for enzyme therapy is the possibility that the liposomes could increase the antigenicity of the enzymes, thus resulting in unwanted immune responses. Liposomes do enhance the antigenicity of many proteins, and they have even been proposed as adjuvants and as a vehicles for vaccines. In the present study we describe a new phenomenon that might help to minimize, or overcome, potential immunological complications associated with enzyme therapy. We have discovered that a small quantity of phosphatidylinositol (PI), mounting to 5% of the total phospholipids in liposomes, can have a potent immunosuppressive effect on expression of a liposomal protein antigen in rabbits. Phosphatidylinositol can also strongly inhibit lymphocyte mitogenesis in tissue culture. Numerous studies have demonstrated that PI is a molecule that may have a central importance in many biological fields, and because of this the present discoveries might have general implications that go beyond immunology alone.

The protein antigen used in this study consisted of cholera toxin (CT) that was bound to its receptor, ganglioside $G_{M1}$. The lipid portion of the ganglioside was imbedded in the lipid bilayer of liposomes, and the liposomes consisted of dipalmitoyl phosphatidylcholine (DPPC). cholesterol, dicetyl phosphate, and, when present, $G_{M1}$ and PI, in molar ratios of 1/0.75/0.11/0.5/0.05. In certain experiments (in FIG. 1) the liposomes consisted entirely of phosphatidylinositol. The liposomes were swollen in 0.15M NaCl such that the DPPC (or PI, when liposomes contained only PI) was 10 mM with respect to the aqueous suspension. The antigen was prepared by mixing 1 ml of swollen liposomes (containing 500 nmoles of $G_{M1}$) with 5 ug of cholera toxin (Sigma Chemical Co., St. Louis, Mo.) at room temperature for 30 min. Separate experiments showed that this amount of CT saturated the $G_{M1}$ binding sites and all of the CT was bound to the liposomes. The bound CT also lacked the ability to activate adenylate cyclase. Antibody activity in rabbit antiserum was assayed by a solid-phase radioimmunoassay. As described before in C. R. Alving, B. Banerji, J. D. Clements and R. L. Richards, in LIPOSOMES AND IMMUNOBIOLOGY, B. H. Tom and H. R. Six, eds (Elsevier/North-Holland, Amsterdam, 1980), p. 67, a dilution curve of the rabbit antiserum was performed in microliter wells containing 1 ug of adsorbed CT. Antibodies bound to the microtiter wells were detected by $^{123}$I-goat antirabbit globulin. RIA units were calculated from a linear portion of the curve as the product of CPM×1/dilution. For the the mitogen assays, splenic lymphocytes from 8-10 week old C57 Bl/6J female mice were stimulated by lipid A, and uptake of $^3H$-thymidine was measured as follows. Splenic lymphocytes were purified over a Ficoll-Hypaque gradient, and washed with RPMI medium. Cultures containing 2×105 cells in 0.2 ml were prepared in RPMI medium 1640 supplemented with glutamine (2 mM), penicillin (100 units/ml), streptomycin (0.1 mg/ml), 5% fetal bovine serum, and 2-mercaptoethylamine (5×10−5M). Both the RPMI 1640 and fetal bovine serum were endotoxin free when tested by Limulus assay. Chloroform-soluble lipid A was dried under nitrogen, solubilized in 0.5% triethylamine, and added to the medium in a final concentration of 0.5 nmoles of lipid A phosphate/ml. Phosphatidylinositol was added in the concentrations per ml of culture indicated in FIG. 1, the cultures were incubated for 72 hours in 5% CO2/95% air at 37° C. Four hours prior to harvesting 1 uCi of $^3H$-thymidine (2 Ci/mmole) was added to each culture, and the cells were harvested on a glass fiber filter with a multiple sample cell harvester. The filters were placed in scintillation vials with 0.5 ml of NCS solubilizer for 24 hours at room temperature. The NCB was then neutralized with glacial acetic acid, and 10 ml of a Liquifluor toluene scintillation cocktail was added. The solution was counted on a Searle model 6880 Mark III liquid scintillation counter.

Figure 4:
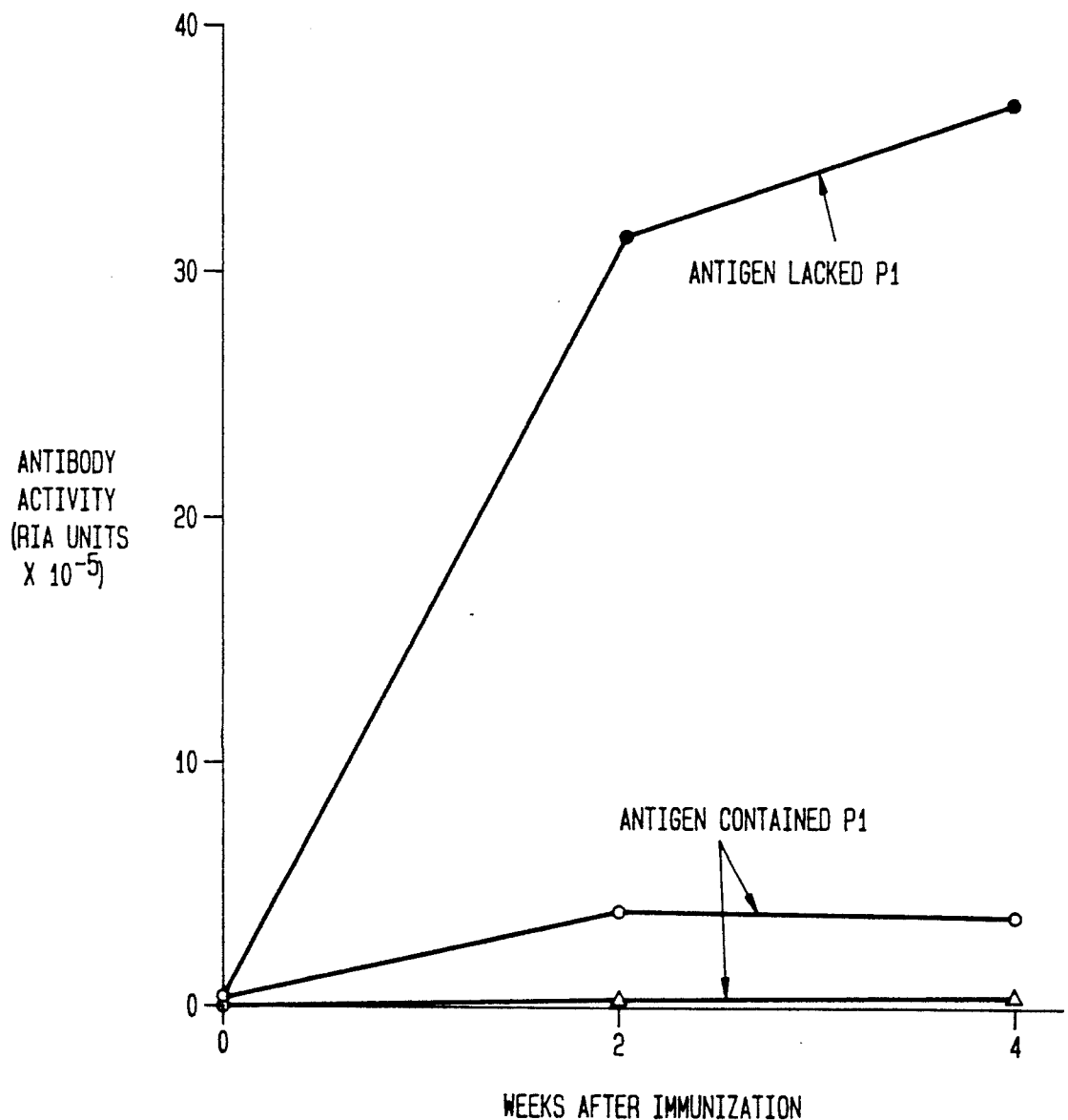
FIG. 4 shows that inclusion of PI as a minor constituent in the liposomes carrying CT resulted in potent immunosuppression in the appearance of humoral antibodies against CT in rabbits.

FIG. 4 shows that inclusion of PI as a minor constituent in the liposomes carrying CT resulted in potent immunosuppression in the appearance of humoral antibodies against CT in rabbits. In a previous study we found that CT attached to liposomal $G_{M1}$ was many times (17-fold) more antigenic than the same amount of CT alone. C. R. Alving, B. Banerji, J. D. Clements and R. L. Richards, in LIPOSOMES AND IMMUNOBIOLOGY, B. H. Tom and H. R. Six, eds. (Elsevier/-North-Holland, Amsterdam, 1980), p. 67. The magnitude of the immune response observed against CT attached to liposomes lacking PI is illustrated by the response of atypical rabbit (FIG. 4). This result was quantitatively consistent with similar results observed by us earlier in other rabbits. Although not shown, the animals illustrated in FIG. 4 were boosted with additional identical antigen after 4 weeks, and suppression of humoral immunity by PI was observed again two weeks after boosting.

In an attempt to provide at least a partial explanation for the immunosuppressive effect of PI (FIG. 4), the influence of PI on mouse lymphocyte mitogenesis was studied. As shown in FIG. 1, activation of mouse lymphocytes by a potent B cell mitogenic stimulus (lipid A) was strongly suppressed by PI. (Footnote 9: The suppressive effects of PI shown in FIG. 1 were identical when performed with PI from animal or plant origin, both obtained from Applied Sciences Laboratory, State College, Pa.). In other experiments, T cell mitogenesis induced by phytohemagglutinin was also suppressed by PI.

Phosphatidylinositol, when present by itself as in FIG. 1, forms liposomes in aqueous suspension. Liposomes consist of closed concentric shells of phospholipid bilayer membranes, and only a fraction of the total PI is exposed on the outer half of the outer lamella of any liposome. Because of this it is difficult to judge the actual amount of the total PI shown on the abscissa in FIG. 1 that participated in suppression of mitogenesis. In addition to simple contact of PI-liposomes with lymphocytes, it is conceivable that there may have been exchange of PI between the PI-liposomes and lymphocytes, or even a small amount of fusion or ingestion of whole PI-liposomes. It should be emphasized that the results observed in FIG. 1 were not related to exchange of cholesterol between liposomes and cells. Cholesterol exchange can affect mitogenesis but under the conditions of our experiments we found equal suppression by PI when the liposomes lacked cholesterol, or contained cholesterol:PI ratios of 1:2 or 1:1 (not shown). Suppression was not observed under any of these conditions when dimyristoyl phosphatidylcholine was substituted for PI.

Although the mechanism of immunosuppression by PI observed in this study is not yet fully understood, enhanced PI turnover has been associated with numerous biological phenomena, and it has been suggested that PI metabolism might have broad biological importance. Enhanced turnover of PI has been observed in both B and T lymphocytes activated by mitogens, V. C. Maino, M. J. Hayman and M. J. Crumpton, *Biochem J.* 146:247 (1975); in activated macrophages, H. M. Ogmundasdottir and D. M. Weir, *Immunology* 37:689 (1979); and indeed in numerous other types of cellular activities initiated by hormones, toxins, antibodies, and various other substances outside the cell, R. H. Michell, *Biochim. Biophys. Acta* 415:81 (1975). It is conceivable that PI added exogenously in liposomal form in our experiments interfered in some way with turnover of PI in immunologically important cells, and thus influenced cellular function. The suppressive phenomena described in this paper should be useful for testing this hypothesis in vitro and in vivo. If the above hypothesis is correct, PI might also have suppressive effects on other cell responses that have been associated with increased PI turnover. Animal PI can supply arachidonic acid for prostaglandin synthesis, R. P. Rubin, L. E. Sink, M. P. Schrey, A. R. Day, C. S. Liao and R. J. Freer, *Biochem. Biophys. Res. Comm.* 90:1364 (1979); P. J. Marshall, J. F. Dixon and L. E. Hokin, *Proc. Nat'l Acad. Sci. U.S.A.* 77:3292 (1980); R. L. Bell, N. L. Baensiger and P. W. Majerus, *Prostaglandins* 20:296 (1980), but plant PI lacks arachidonic acid, R. H. Michell, *Biochim. Biophys. Acta* 415:81 (1975). In the present experiments animal and plant PI were equally suppressive, thus eliminating arachidonic acid as a critical factor in the mechanism.

Although increased PI metabolism has been observed in conjunction with numerous biological activities, to date any direct role of PI in the biological functions per se has not been established. Our results suggest the possibility that PI itself might play a central and direct role in modulating certain important cellular activities. Based on the broad literature implicating PI as a possible factor in a wide spectrum of functions, we suggest that our results might also have relevance in fields other than immunology. Liposomal PI might be a central molecule that directly suppresses or influences functions of various cells. These results raise the possibility that the use of small amounts of PI in liposomes might suppress unwanted immune responses against enzymes or other proteins, or even drugs, encapsulated within liposomes for therapeutic purposes.

It should also be noted that in the Note 9 that refers to FIG. 2 of the manuscript it is stated the suppressive effects of PI were identical when performed with PI from animal or plant origin. We did discover shortly after this work was completed that there was a marked difference between the activities of animal and plant PI. The discrepancy sometimes arises because the PI that is obtained from animal sources is frequently contaminated, and a particularly vexing contamination, and the contaminant that is most commonly found, is lysoPI (Jett, M. and Alving, C. R., Tumoricidal effects of liposomes containing phosphatidylinositol or phosphatidylcholine, Meth. Enzymol. 141:459–466, 1987). LysoPI Consists of the breakdown product of PI consisting of PI that lacks the sn-2 fatty acid. Our research has revealed that the most likely mechanism by which phosphatidyl compounds exert their biological effect is through the production of lysophosphatidyl compounds (Jett, M. and Alving, C. R., Phospholipase A2 substrates: a novel. approach to cancer chemotherapy. In, "Liposomes as Drug Carriers", G. Gregoriadis, editor, John Wiley & Sons, London, 1988, pp. 419–429). Therefore it is likely that the batch of animal PI that was tested was contaminated with lysoPI and this was the source of the activity in the animal PI. As shown in the next example, animal PI that is free of lysoPI lacks suppressive activity against mitogenic stimulus.

EXAMPLE 2

C57B1/6J mouse spleen cells were purified by Ficoll-Hypaque gradient centrifugation, washed three times with RPMI 1640 medium supplemented with 100 ug streptomycin, 100 units of penicillin/ml, $5 \times 10-5M$ 2-mercaptoethanol and 5% fetal bovine serum. Microcultures were prepared by adding to a well of a microtiter plate, 0.1 ml containing $5 \times 10\ 5$ viable spleen lymphocytes, 0.05 ml containing 0.1 nmole lipid A phosphate (prepared from *S. flexneri*LPS) and 0.05 ml containing various amounts of liposomes composed of soybean or bovine brain phosphatidylinositol and cholesterol in a molar ratio of 1:05. Cultures were incubated for 3 days at 37 C and under 5% $CO_2$ and air atmosphere. Cultures were pulsed 4 hours before harvesting with 1 uCi of tritiated thymidine. Each point is the geometric mean of quadruple cultures +1SE.

EXAMPLE 3

C57B1/6J mouse spleen cells were purified by Ficoll-Hypaque gradient centrifugation, washed three times with a RPMI 1640 medium supplemented with 100 ug streptomycin. 100 units of penicillin/ml. $5 \times 10-5M$ 2-mercaptoethanol and 5% fetal bovine serum. Microcultures were prepared by adding to a well of a microtiter plate, 0.1 ml containing $5 \times 10\ 5$ viable spleen lymphocytes, 0.05 ml containing 0.8 ug of PHA and 0.05 ml containing various amounts of liposomes composed of soybean or bovine brain phosphatidylinositol and cholesterol in a molar ratio of 1:05. Cultures were incubated for 3 days at 37 C and under 5% CO2 and air atmosphere Cultures were pulsed 4 hours before harvesting with luCi of tritiated thymidine. Each point is the geometric mean of quadruple cultures +1SE.

What is claimed is:

1. A method for inhibiting mitogenic transformation of normal mammalian cells, comprising the step of contacting normal cells, in a mammalian subject not harboring transformed cells, with a transformation-inhibiting amount of diacyl phosphatide.

2. A method according to claim 1, wherein said phosphatide is contacted in the form of a liposome.

3. A method according to claim 2, wherein said liposome comprises lipid A.

4. A method according to claim 1, wherein said sn2-acyl group is linoleoyl.

5. A method according to claim 4, wherein said diacyl is dilinoleoyl.

6. A method according to claim 1, wherein said sn2-acyl group is arachidonyl.

7. A method according to claim 1, wherein said cells are human cells.

8. A method according to claim 1, wherein said plant composition is a purified soybean composition.

9. A method according to claim 1, wherein the sn2-acyl group of said diacyl phosphatide is a polyunsaturated fatty acid.

10. A method according to claim 1, wherein said contacting occurs in the substantial absence of non-phosphatidic fatty acid esters that have fewer than two olefinic sites of unsaturation in the fatty acid of said esters.

11. A method according to claim 1, wherein the sn2-acyl group of said diacyl phosphatide is a polyunsaturated fatty acid, wherein said contacting occurs in the substantial absence of non-phosphatidic fatty acid esters that have fewer than two olefinic sites of unsaturation in the fatty acid of said esters.

* * * * *